United States Patent [19]

Lubkowitz et al.

[11] Patent Number: 5,057,126
[45] Date of Patent: Oct. 15, 1991

[54] GAS CHROMATOGRAPHY

[76] Inventors: Joaquin A. Lubkowitz, 100-C Nightingale La., Gulf Breeze, Fla. 32561; Harold K. Bellows, 830 Bellows Ct., Walnut Creek, Calif. 94598

[21] Appl. No.: 659,111
[22] Filed: Feb. 25, 1991
[51] Int. Cl.$^5$ .............................................. B01D 15/08
[52] U.S. Cl. ......................................... 55/67; 55/197; 55/386
[58] Field of Search ..................... 55/67, 197, 208, 386

[56] References Cited

U.S. PATENT DOCUMENTS

| | | | |
|---|---|---|---|
| 3,366,149 | 1/1968 | Taft et al. | 55/197 X |
| 3,719,084 | 3/1973 | Walker | 55/197 X |
| 3,881,892 | 5/1975 | Gehrke et al. | 55/67 |
| 4,003,257 | 1/1977 | Fletcher et al. | 55/197 X |
| 4,035,168 | 7/1977 | Jennings | 55/197 X |
| 4,180,389 | 12/1979 | Paul | 55/197 X |
| 4,699,768 | 10/1987 | Weiss | 55/197 X |

Primary Examiner—Robert Spitzer
Attorney, Agent, or Firm—Kelly O. Corley

[57] ABSTRACT

In gas chromatography wherein only the more volatile components of a multi-component sample are of interest, the sample is injected into a hot vaporization chamber containing a packing material. An inert carrier gas sweeps the resulting vaporized gases through a second packed column at a lower temperature than the vaporization chamber. After the more volatile components of interest have passed an intermediate conduit, a backflushing stream is fed sequentially through the second column and the vaporization chamber, exhausting through a vent. Simultaneously with opening of the vent, and beginning of the backflushing, a further stream continues to drive the portion of the first stream containing the more volatile components toward and through a chromatographic analytic column.

11 Claims, 1 Drawing Sheet

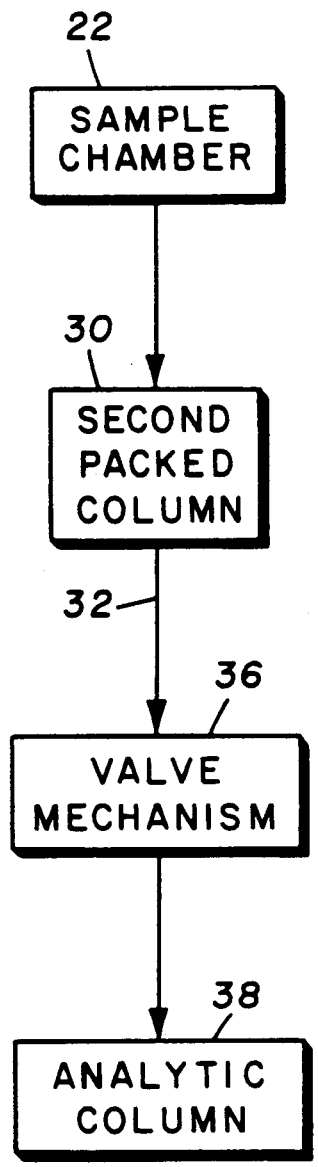
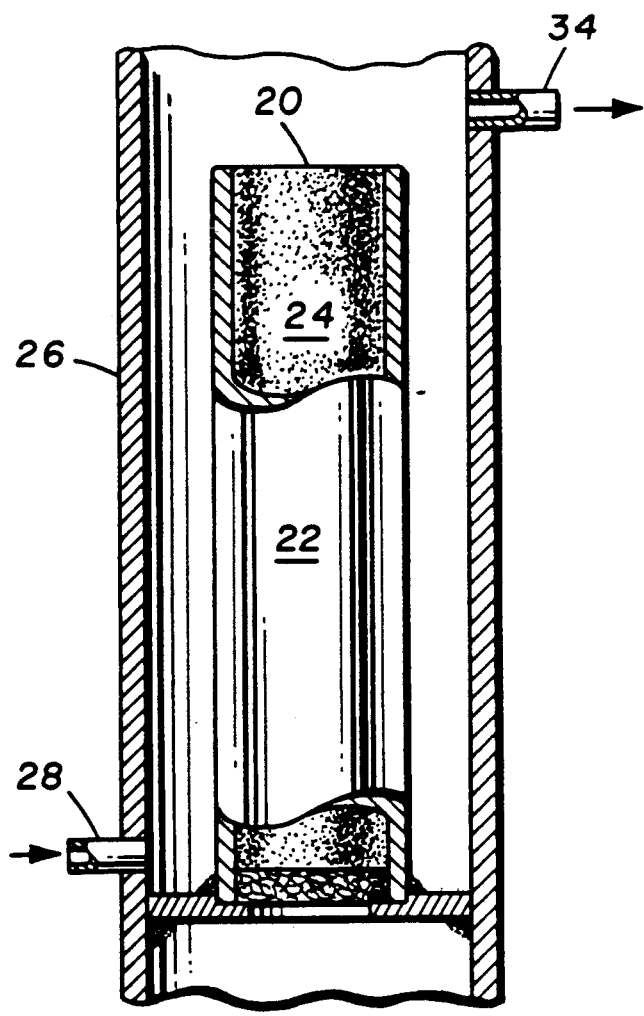
FIG.1.
FIG.2.

GAS CHROMATOGRAPHY

The invention relates to the art of gas chromatography, and more particularly to such chromatography for rapidly determining the volatiles content of a multicomponent sample.

Gas chromatography is a well known technique for fractionating and determining the relative amounts of various components in a sample containing a mixture of compounds of differing volatilities. In the conventional such process, the sample is vaporized and the entire resulting quantity of gases is passed through an analytical chromatography column.

Situations arise wherein there is little or no interest in determining the amount of the less volatile compounds, or wherein the less volatile components might foul the analytical chromatography column. Provision of a process wherein only the more volatile components of interest would accordingly lead to increased productivity of the analytical chromatography column, and would avoid damage to the column.

According to the invention, there is provided such a process wherein only the desired more volatile components are passed through the analytical column, the less volatile components be backflushed prior to entry into the analytical column.

According to a principal aspect of the invention, there is provided a chromatagraphic process for rapidly determining the volatiles content of a multicomponent sample, the process comprising injecting the sample at an injection point into a heated sample chamber containing a packing material whereby the sample is vaporized, entraining the vaporized sample in a first stream of inert carrier gas flowing at a given volumetric flow rate sequentially through the chamber, a second packed column maintained at a lower temperature than the chamber, an intermediate conduit, and a chromatographic analytical column, the second packed column preferentially permitting passage therethrough of a first portion of the first stream having entrained therein more volatile components while preferentially retarding a second portion of the first stream having entrained therein less volatile components of the sample. When the first portion of the first stream having entrained therein the more volatile components has passed the intermediate conduit, substantially simultaneously a vent is opened near the injection point, the first portion of the first stream continues to be driven toward and through the chromatographic analytical column, and a backflush stream of inert carrier gas flows sequentially through the second packed column and the heated sample chamber to exit through the vent, whereby the backflush stream entrains and flushes the second portion of the first stream and the less volatile components out through the vent.

According to another aspect of the invention, the backflush is maintained throughout a substantial portion of the period during which the more volatile components are passing through the analytical column, and preferably throughout the entire analytical process.

According to another aspect of the invention, the second column is operated substantially isothermally.

According to another aspect of the invention, the analytical column is operated at a temperature lower than the temperature of the heated sample chamber.

According to another aspect of the invention, the analytical column is operated substantially isothermally.

According to another aspect of the invention, the analytical column comprises a capillary tube through which the entrained more volatile components pass prior to analysis and are separated therein according to boiling point.

According to another aspect of the invention, the first portion of the first carrier gas stream while passing through the analytical column has substantially the same volumetric flow rate as the given volumetric flow rate.

According to another aspect of the invention, the multicomponent sample comprises petroleum.

According to another aspect of the invention, the more volatile components comprise hydrocarbons having less than ten carbon atoms, and preferable less than eight carbon atoms.

According to another aspect of the invention, the sample chamber is contained in a heated vessel, the sample chamber comprising an open upper end through which the sample is introduced and through which the carrier gas enters and flows through the sample chamber when the sample is introduced, the vent being so located that when the vent is opened the first carrier gas stream thereafter flows across the open end and out through the vent, the volumetric flow rate of the first carrier gas stream being preferably increased such that a turbulent flow is produced across the open end when the vent is open and the turbulent flow entrains the backflush stream while flowing out the vent.

Other aspects will in part appear hereinafter and will in part be apparent from the following detailed description taken together with the accompanying drawing, wherein FIG. 1 is a block diagram illustrating the process of the invention, and FIG. 2 is a side elevational view, partly broken away, of the preferred heated sample chamber according to the invention.

As illustrated in FIG. 1, the sample to be analyzed is injected, as by hypodermic needle, at an injection point in the open upper end 20 of sample chamber 22 and is there vaporized. Sample chamber 22 is filled with a suitable packing material 24 such as Chromasorb P, 80–100 mesh size, available from Johns Manville, having coated thereon 30% by volume Union Carbide Chemicals W982 silicone oil. The preferred sample chamber is a tube of stainless steel 3 inches (7.62 mm) long and has an inner diameter of 4 mm. Chamber 22 is surrounded by heated vessel 26 maintained at a high temperature so as to rapidly evaporate the volatile materials of interest, such as 240 degrees C. in the present specific instance wherein it is desired to determine the amount of hydrocarbons having up to 8 carbon atoms in a sample of petroleum. The bottom outer periphery of sample chamber 22 is sealed to the inner surface of vessel 26.

The vaporized sample is entrained in a first stream of inert carrier gas flowing downwardly through chamber 22. As illustrated in FIG. 2, the first stream preferably enters vessel 26 at a point 28 near the bottom of the outer surface of sample chamber 22, and flows upwardly through the annular space separating sample chamber 22 and vessel 26 before entering the open upper end of sample chamber 22 and thereafter flowing downwardly through packing 24. This preheats the inert carrier gas before the carrier gas contacts and entrains the vaporized sample.

The first stream of carrier gas leaving the bottom of sample chamber 22 flows next through second packed column 30 maintained at a lower temperature than sample chamber 22, in this specific example at 40 degrees C. Second column 30 is preferably a stainless steel tube 13 cm in length and having an inner diameter of 3.1 mm, and is packed with Chromasorb G, 80-100 mesh particle size. The Chromasorb G is coated with 5% by volume Ohio Valley 101 silicone oil. Principle functions of second packed column 30 are to separate the volatile materials of interest entrained in a first portion of the first stream from the higher boiling compounds entrained in a second portion of the first stream, to partially separate the more volatile compounds from one another, and to introduce a small delay. The first portion of the first stream containing the more volatile compounds next passes through intermediate conduit 32. When has occurred, substantially simultaneously vent 34 in the wall of vessel 26 near the injection point is opened and valve mechanism 36 is actuated. Valve mechanism 36 is constructed and arranged so as to supply a backflush stream flowing sequentially through second column 30 and sample chamber 22, then out vent 34, entraining and removing from second packed column 30 and sample chamber 22 the less volatile components of the sample contained in the second portion of the first stream of carrier gas. Valve mechanism 36 also substantially simultantously supplies a further carrier gas stream to continue driving the first portion of the first stream and its entrained more volatile sample components toward and through chromatographic analytic column 38 wherein the various sample components are separated and measured by known means. An optional further packed column may be positioned between valve mechanism 36 and analytic column 38. Analytic column 38 is preferably in the form of a capillary, for example thirty meters long and having a diameter of 0.53 mm.

It is preferred to maintain all described columns isothermally, for example at 40 degrees C., while heated sample chamber 22 is preferably operated at about 240 degrees C. when analyzing petroleum for compounds having less than ten carbon atoms.

It is likewise preferred to increase the volumetric flow rate of the first stream during the backflush operation, providing a turbulent flow across open end 20 of sample chamber 22. This assists the backflushing and removal of the less volatile components. The backflushing preferably continue throughout the entire period during which the more volatile components are being analyzed. As an example, the volumetric flow rate through analytic column 38 may be maintained at about 21.4 ml/minute, while the volumetric flow rate of the turbulent flow across open end 20 of chamber 22 may be several times that amount. Selection of specific flow rates is within the scope of one having ordinary skill in the chromatographic analysis art.

Advantageously, the various streams are supplied through parallel volume and pressure controllers in order to minimize flow fluctuations during operation of valve mechanism 36.

I claim:

1. A chromatagraphic process for rapidly determining the volatiles content of a multicomponent sample, said process comprising:
   a. injecting said sample at an injection point into a heated sample chamber whereby said sample is vaporized, said chamber containing a packing material;
   b. entraining said vaporized sample in a first stream of inert carrier gas flowing at a given volumetric flow rate sequentially through said chamber, a second packed column maintained at a lower temperature than said chamber, an intermediate conduit, and a chromatographic analytical column, said second packed column preferentially permitting passage therethrough of a first portion of said first stream having entrained therein more volatile components while preferentially retarding a second portion of said first stream having entrained therein less volatile components of said sample; and
   c. when said first portion of said first stream having entrained therein said more volatile components has passed said intermediate conduit, substantially simultaneously:
      (1) opening a vent near said injection point,
      (2) continuing driving said first portion of said first stream toward and through said chromatographic analytical column; and
      (3) introducing a backflush stream of inert carrier gas sequentially through said second packed column and said heated sample chamber to exit through said vent, whereby said backflush stream entrains and flushes said second portion of said first stream and said less volatile components out through said vent.

2. The process defined in claim 1, wherein said back flush is maintained throughout a substantial portion of the period during which said more volatile components are passing through said analytical column.

3. The process defined in claim 1, wherein said second column is operated substantially isothermally.

4. The process defined in claim 1, wherein said analytical column is operated at a temperature lower than the temperature of said heated sample chamber.

5. The process defined in claim 1, wherein said analytical column is operated substantially isothermally.

6. The process defined in claim 1, wherein said analytical column comprises a capillary tube through which said entrained more volatile components pass prior to analysis and are separated according to boiling point.

7. The process defined in claim 1, wherein said first portion of said first carrier gas stream while passing through said analytical column has substantially the same volumetric flow rate as said given volumetric flow rate.

8. The process defined in claim 1, wherein said multicomponent sample comprises petroleum.

9. The process defined in claim 8, wherein said more volatile components comprise hydrocarbons having less than ten carbon atoms.

10. The process defined in claim 9, wherein said more volatile components comprise hydrocarbons having less than eight carbon atoms.

11. The process defined in claim 1, wherein said sample chamber is contained in a heated vessel, said sample chamber comprising an open upper end through which said sample is introduced and through which said carrier gas enters and flows downwardly through said sample chamber when said sample is introduced, said vent being so located that when said vent is opened said first carrier gas stream thereafter flows across said open end and out through said vent, the volumetric flow rate of said first carrier gas stream being selected such that a turbulent flow is produced across said open end when said vent is open and said turbulent flow entrains said backflush stream while flowing out said vent.

* * * * *